United States Patent [19]

Schnurbusch et al.

[11] 4,317,900
[45] Mar. 2, 1982

[54] ISOCYANATOMETHYL GROUP CONTAINING UREA DERIVATIVES OF 3(4), 8(9)-DIISOCYANATOMETHYLTRICYCLO [5.2.1.0$^{2,6}$] DECANE, METHOD FOR THEIR PRODUCTION AS WELL AS THEIR USE FOR PRODUCING POLYURETHANE ELASTOMERS

[75] Inventors: Horst Schnurbusch; Rainer Gras; Elmar Wolf, all of Herne, Fed. Rep. of Germany

[73] Assignee: Chemische Werke Huls Aktiengesellschaft, Kreis Recklinghausen, Fed. Rep. of Germany

[21] Appl. No.: 173,619

[22] Filed: Jul. 30, 1980

[30] Foreign Application Priority Data

Aug. 11, 1979 [DE] Fed. Rep. of Germany ....... 2932646

[51] Int. Cl.$^3$ .................. C08G 18/10; C07C 119/045
[52] U.S. Cl. ............................. 528/59; 260/453 AP; 260/453 P; 528/60; 528/65; 528/66; 521/159
[58] Field of Search ................... 260/453 AP, 453 P; 528/59, 60, 65, 66

[56] References Cited

U.S. PATENT DOCUMENTS 3,470,248  9/1969  Brotherton et al. ...... 260/453 AP X
3,952,040  4/1976  Schnurbusch et al. ......... 260/453 A
4,151,194  4/1979  Wu et al. ................. 260/453 AP X Primary Examiner—Dolph H. Torrence
Attorney, Agent, or Firm—Oblon, Fisher, Spivak, McClelland & Maier

[57] ABSTRACT

Urea derivatives containing isocyanatomethyl groups of 3(4), 8(9)-diisocyanatomethyltricyclo [5.2.1.0$^{2,6}$] decane of the formula OCN—H$_2$C—[R—CH$_2$—NH—CO—NH—CH$_2$-]$_n$—R—CH$_2$—NCO, in which R is

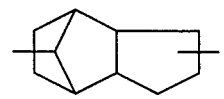

and n=1–5.

6 Claims, No Drawings

ISOCYANATOMETHYL GROUP CONTAINING UREA DERIVATIVES OF 3(4), 8(9)-DIISOCYANATOMETHYLTRICYCLO [5.2.1.0$^{2,6}$] DECANE, METHOD FOR THEIR PRODUCTION AS WELL AS THEIR USE FOR PRODUCING POLYURETHANE ELASTOMERS

BACKGROUND OF THE INVENTION

1. Field of the Invention

The present invention relates to urea derivates containing isocyanatomethyl groups of the 3(4), 8(9)-diisocyanatomethyltricyclo-[5.2.1.0$^{2,6}$] decane, hereinafter referred to as TCDI, as well as their production and use.

2. Description of the Prior Art

Cold-hardened, highly elastic polyurethane masses have become very important in recent years. This is due particularly to their outstanding characteristics such as friction wear resistance, chemical resistance, toughness, long-term elasticity, durability and their resistance to cold temperatures.

A urea derivate of isophorondiisocyanate described in the DE-OS 23 41 065 can be used advantageously for such solvent-free polyurethane elastomers. This urea has the disadvantage, however, that its isocyanate groups are very slow to react. More or less large amounts of catalysts are indispensable to harden this urea derivate with a corresponding polyol component. However, these catalysts not only accelerate the reaction between NCO- and HO-groups, they also impair, even if only slightly, the hydrolysis stability of the hardened polyurethane system.

SUMMARY OF THE INVENTION

The goal of the present invention is to produce a diisocyanate having the advantages of the isophorondiisocyanate urea derivate but lacking its disadvantages.

The objects of the invention are urea derivates containing isocyanatomethyl groups of 3(4), 8(9)-diisocyanatomethyltricyclo [5.2.1.0$^{2,6}$] decane (TCDI) of the formula OCN—H$_2$C—[R—CH$_2$—NH—CO—NH—CH$_2$]$_n$-R—CH$_2$—NCO, in which R is

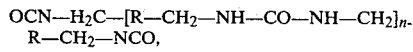

and n=1–5. Furthermore, it was discovered that these compounds can be easily obtained by mixing the 3(4), 8(9)-diisocyanatomethyltricyclo [5.2.1.0$^{2,6}$] decane (TCDI)

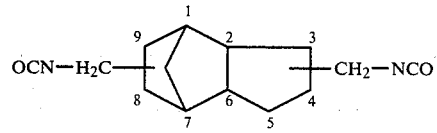

with less than equivalent amounts of water, by mixing TCDI with water in a molar ratio of 12-2.0:1, preferably 6-3:1, at 60°–110° C., possibly in the presence of a catalyst and/or an inert solvent. In addition to the escaping CO$_2$ the reaction products of TCDI are compounds of the general formula above.

Description of the Preferred Embodiments

The reaction product can contain non-reacted TCDI (n=0) as well as reaction products for which n is also up to 8. Normally n lies in the middle between 1 and 5 for the reaction product.

It is—as is the reaction product of isophorondiisocyanate with water—soluble in excess diisocyanate as well as in a series of polyurethane solvents. The TCDI, partially mixed with water according to the invention, is characterized by its high reactivity as well as its low viscosity. It is surprisingly well suited for the production of solvent-free polyurethane elastomers characterized by good color stability and continued tear growth resistance.

Urea derivates of TCDI containing isocyanatomethyl groups of the general formula above are produced as follows: by slowly adding water to the TCDI warmed to 60°–110° C. in a molar ratio TCDI:water of 12 to 2.0:1. Particularly interesting products are produced with molar ratios between 6-3:1.

It has proved to be especially advantageous if the water is added as a vapor. This is easiest to carry out by introducing a stream of water-saturated nitrogen through the TCDI. With this method variation higher molecular urea derivates (n>2) are extensively suppressed.

Metal organic compounds or carboxylic acid salts of Sn, Pb, Zn, Fe or Mn are suitable as catalysts for converting the TCDI with water. Examples of such catalysts are di-n-butylstannousdilaurate and -diacetate, stannous (II)-octate or zinc octate. Also, tertiary amines such as 1.4-diazabicyclooctane [2.2.2] can be used alone or in mixtures as catalysts with the compounds mentioned above. The compounds according to the invention can be converted without difficulty to polyurethane elastomers with the most varied compounds containing hydroxyl groups. In contrast to the urea derivate of the isophorondiisocyanate described in the DE-OS 23 41 065, no catalyst is needed to harden the TCDI derivates at room temperature.

The following compounds containing hydroxyl groups are possible as conversion components:

Polyester polyols, condensation products of aliphatic and/or aromatic polycarboxylic acids, such as adipic acid, azelic acid, sebacic acid, dodecane dicarboxylic acid, phthalic acid, isophthalic acid, tetrahyrophthalic acid, hexahydrophthalic acid among others; and glycols, such as ethylene glycol, diethylene glycol, triethylene glycol, propane diol-1.3(1.2), butane diol-1.4(1.3), pentanediol-1.5, 3-methylpentane diol-1.5, hexane diol-1.6, 2.2.4-(2.4.4.)-trimethylhexane diol-1.6, neopentyl glycol, hydroxypivalineneopentylglycolester, 3(4), 8(9)-dihydroxymethyl-tricyclo-[5.2.1.0$^{2,6}$]-decane, dimethylolcyclohexane among others; and polyols, such as 1.1.1-trimethylolethane, 1.1.1-trimethylolpropane, glycerine, hexanetriol-.1.2.6 among others, polylactone polyester polyols; polymerization products of lactones, such as ϵ-caprolacton, ϵ-methylcaprolacton, valerolactone among others; polyether polyols, which can be obtained by anionic polymerization, copolymerization and block polymerization of alkylene oxides, such as ethylene oxide, propylene oxide or butyleneoxide, with di- or polyfunctional alcohols, such as butane diol-1.4, 1.1.1-trimethylol ethane, 1.1.1-trimethylol propane, glycerine, pentaerythrite and sorbite or, respectively, their alkali alcoholates or with amines, such as methylamine and ethylenediamine as starting components or by cationic polymerization or, respectively, copolymerization of cyclic ethers, such as tetrahydrofurane, ethylene oxide or propylene oxide with acid catalysts, such as boron trifluoride etherate or by polycondensation of glycols that are polycondensable on losing water, such as hexanediol-1.6, in the presence of acid etherification catalysts, such as p-toluol sulphonic acid.

All of these compounds can be used separately or in mixtures. (Compare also the examples.) Isocyanates and compounds containing hydroxyl groups are used in such amounts that the NCO/OH-group ratio is 0.9–1.1:1, preferably 0.95–1.05:1.

Besides the reaction partners, the auxiliary and additive materials common polyurethane chemistry can be used if necessary:

1. Fillers that improve properties Quarz powder, chalk, slate flour, aluminum trioxide hydrate and fabrics, fibers, glass, textile- and rubber parings.
2. Water adsorbers such as alkali-alumino-silicate with needle-zeolite structure. If removing the gas and moisture from the reaction mixture by vacuum alone is not successful zeolite can be added to the reaction mass in order to produce bubble-free polyurethane-elastomers.
3. Reactive thinners such as aryloxyalkanols, e.g. thinned PU (Produced by Bayer AG), a reaction product of phenol and propylene oxide.
4. Flame inhibitors, softeners, pigments, stabilizers, air removers, wetting agents, etc.

The components can be manually or mechanically mixed. Mechanical mixing is advisable if continuous processing is forseen.

The mixtures produced according to the invention can be applied by the various known methods such as pouring, injecting, painting, squeegee and flatting with the customary tools and machines. Having generally described the invention, a more complete understanding can be obtained by reference to certain specific examples, which are provided herein for purposes of illustration only and are not intended to be limiting unless otherwise specified.

EXAMPLES

A. Production of polyol components 1. 292 g adipic acid, 104 g neopentyl glycol, 118 g 1,6-hexanediol and 134 g 1,1,1-trimethylolpropane were esterified. After 4 moles of water were separated, the esterification was continued to an acid number of <2 mg KOH/g with the addition of 0.1% by weight of di-n-butylstannous oxide (DBTO). By evacuating at 13.33 Pa at 180° C. for 20–30 minutes a product was produced with a water content of <0.1% by weight, a hydroxyl number of 270–285 mg KOH/g and a viscosity (at 25° C.) of ca. 500 Pa.s. 2. 2685 g of adipic acid, 944 g hexane diol-1.6, 1650 g triethyleneglycol and 268 g 1.1.1.-trimethylol propane were esterified with an added catalyst as in A1. The polyester produced in this manner had a final acid number of <2 mg KOH/g and a viscosity (at 25° C.) of ca. 300 Pa.s.

B. Production of the isocyanate components 1. 9.4 parts by weight of water were added to 1014 parts by weight TCDI at 80° C. within 6 h. After the end of $CO_2$-development, ca. 12 1 $CO_2$ escape, heat was continued at 80° C. for another hour. The diisocyanate containing urea groups produced in this manner had an NCO-content of 30.2% and at room temperature a viscosity of 15 Pa.s.
2. A water saturated stream of nitrogen was passed through 1014 parts by weight of TCDI at 80° C. After 9.4 parts by weight of water were added in this manner, the nitrogen stream was stopped and it was heated for ca. another 1 hour at 80° C. The diisocyanate containing urea groups produced in this manner had an NCO-content of 30.2% and at room temperature a viscosity of 11.5 Pa.s.
3. 14.7 parts by weight of water were added in a manner analogous to that in B1 at 80° C. to 1023 parts by weight of TCDI. After $CO_2$-development had stopped (ca. 18 1) the reaction product had an NCO-content of 28% and a viscosity of 250 Pa.s at room temperature.
4. If 1023 parts by weight of TCDI are reacted with 14.7 parts by weight of water according to the reaction product of B2, the reaction product has an NCO-content of 28% and a viscosity at room temperature of ca. 230 Pa.s.

C. Use of TCDI derivates containing isocyanatomethyl groups for the production of polyurethane-elastomers To produce the standard examination body for determining the mechanical characteristics and for stability experiments, component A, consisting of the polyester with zeolite paste (50% suspension of molecular sieve zeolite in castor oil), stabilizers, thinner PU (monoalcohol from the Bayer Co. made from phenol and propylene oxide), fillers defoamers and, under certain circumstances, softeners (butylbenzylphthalate; produced by Bayer) and with pigments was mixed together at 20° C. to 80° C. and then degassed until free of bubbles. Then component B (isocyanate component = derivate of TCDI containing isocyanatomethyl groups) was added to component mixture A, homogenized and degassed until free of bubbles. The mixtures remained pourable for 20–40 min. and hardened within 24 hours to a cross-linked polyurethane plastic. The OH/NCO-group ratio was 1:1 in all examples. The following table shows the mechanical characteristics of some polyurethane-elastomers:

| Recipe | Dimension | I | II | III | IV | V | VI | VII | VIII |
|---|---|---|---|---|---|---|---|---|---|
| Component A | | | | | | | | | |
| Polyester according to A 1 | Parts by Weight | — | — | — | — | 305.33 | — | — | 295.66 |
| Polyester according to A 2 | Parts by Weight | 368.42 | 424.71 | — | — | — | 361.09 | — | — |
| Polyester according to A 3 | Parts by Weight | — | — | 361.13 | 281.36 | — | — | 273.76 | — |

| Recipe | Dimension | I | II | III | IV | V | VI | VII | VIII |
|---|---|---|---|---|---|---|---|---|---|
| Slate flour | Parts by Weight | 430 | 375 | 380 | 370 | — | 430 | 370 | — |
| Titanium dioxide | Parts by Weight | 20 | — | 20 | — | — | 20 | — | — |
| Kaolin | Parts by Weight | — | — | — | 65 | — | — | 65 | — |
| Quartz powder | Parts by Weight | — | — | — | — | 450 | — | — | 450 |
| Chromoxide green | Parts by Weight | — | 25 | — | 20 | — | — | 20 | — |
| Chromoxide yellow | Parts by Weight | — | — | — | 5 | — | — | 5 | — |
| Thinner PU | Parts by Weight | 30 | 20 | 20 | 10 | — | 30 | 10 | — |
| Needle-zeolite paste | Parts by Weight | 30 | 30 | 30 | 50 | 30 | 30 | 50 | 30 |
| Butylbenzylphthalate | Parts by Weight | — | — | — | 50 | — | — | 50 | — |
| UV stabilizer | Parts by Weight | 2,5 | 2,5 | 2,5 | 2,5 | — | 2,5 | 2,5 | — |
| Oxidation stabilizer | Parts by Weight | 2,5 | 2,5 | 2,5 | 2,5 | — | 2,5 | 2,5 | — |
| Defoamer | Parts by Weight | 0.5 | 0.5 | 0.5 | 0.5 | 0.5 | 0.5 | 0.5 | 0.5 |
| Component B | | | | | | | | | |
| isocyanate according to B1 | Parts by Weight | 116.08 | 119.79 | 183.37 | 143.14 | 214.17 | — | — | — |
| isocyanate according to B3 | Parts by Weight | — | — | — | — | — | 123.41 | 150.74 | 223.84 |
| Mechanical Characteristics | | | | | | | | | |
| Hardness according to DIN 53 505 | | | | | | | | | |
| Shore A | | 42 | 53 | 79 | 81 | 99 | 45 | 87 | 98 |
| Shore B | | — | — | 30 | 34 | 75 | — | 36 | 77 |
| Pull test according to DIN 53 504 | | | | | | | | | |
| Break tension | N/mm$^2$ | 1.38 | 1.41 | 4.2 | 2.9 | 25.8 | 1.47 | 3.1 | 26.7 |
| Break elongation | % | 420 | 320 | 150 | 115 | 20 | 400 | 100 | 18 |
| Tear growth test according to DIN 53 507 | | | | | | | | | |
| tear growth resistance | N/mm | 4.5 | 4.0 | 3.1 | — | — | 4.9 | — | — |
| Tear growth resistance according to DIN 53 515 | | | | | | | | | |
| according to Graves | N/mm | 9 | 8.1 | 5.8 | 9.4 | 56.8 | 9.6 | 9.7 | 57.2 |
| Abrasion wear according to DIN 53 516 | | | | | | | | | |
| Volume loss | mm$^3$ | 80 | 50 | 45 | 51 | 60 | 75 | 53 | 57 |
| Compression strain reserve according to DIN 53 517 | | | | | | | | | |
| 70 h/20° C. | % | 9 | 9 | 4 | 9 | — | 8 | 5 | — |

With Zenotest 450 LF (of the company Original Hanau) the test bodies remain almost unchanged after 2000 hours of testing. The Shore hardnesses and tensile strength were slightly lower and the elongation slightly greater. Tear growth resistance, abrasion wear and compression strain reserve remained nearly unchanged.

The solvent-free polyurethane-elastomers produced in this manner are primarily used for floor coverings for industry and sports installations, for school grounds and the like. They are also suitable for use as adhesives, cement filters, sealants and calking compounds. They have also shown promise in the production of pressure drums. Another application area is as a coating for substrates and fabrics of all types, e.g. for the manufacture of transport belts, carpet backings, and mats. In addition they can be used to produce floor tiles and foam sealants.

If solid urea materials are produced in the hydrolysis of TCDI, it is advantageous to use solvents for the reaction. Suitable PUR solvents are those that are inert against NCO-groups, such as aromates, hydroaromates, and chlorinated aromates, such as benzol, toluol, diisopropylbenzol, chlorobenzene and O-dichlorobenzene, among others. Having now fully described the invention, it will be apparent to one of ordinary skill in the art that many changes and modifications can be made thereto without departing from the spirit or scope of the invention as set forth herein.

What is claimed as new and intended to be covered by letters patent of the United States is:

1. Urea derivatives containing isocyanatomethyl groups of 3(4), 8(9)-diisocyanatomethyltricyclo[5.2.1.0$^{2,6}$] decane of the formula

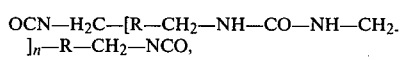

in which R is

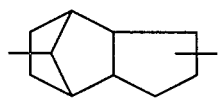

and n=1–5.

2. A method for the production of urea compounds containing isocyanatomethyl groups of the formula:

OCN—H₂C—[R—CH₂NHCONHCH₂]$_n$—R—CH₂—NCO, wherein R is

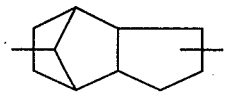

and n is 1 to 5, comprising:

reacting 3(4), 8(9)-diisocyanatomethyltricyclo [5,2,1,0$^{2,6}$] decane with water in a molar ratio of 12-2.0:1 at a temperature of 60°-110° C., said water being supplied as a stream of water saturated nitrogen through the diisocyanate reactant until an amount of water within the stated ratio has been added.

3. The method of claim 2, wherein said diisocyanate is reacted with water in a molar ratio of 6-3:1.

4. The method of claim 2, wherein said temperature ranges from 80°-100° C.

5. The method of claim 2, which further comprises conducting said reaction in the presence of a catalyst.

6. A method of producing polyurethane elastomers free of solvents comprising mixing the urea derivative containing isocyanatomethyl groups according to claim 1 with hydroxyl group-containing compounds.

* * * * *